United States Patent
Sigsworth et al.

(10) Patent No.: US 10,569,055 B1
(45) Date of Patent: Feb. 25, 2020

(54) MEDICAL TUBING MANAGEMENT APPARATUS

(71) Applicants: Joshua Sigsworth, Abington, MA (US); Matthew Gingras, Middletown, CT (US)

(72) Inventors: Joshua Sigsworth, Abington, MA (US); Matthew Gingras, Middletown, CT (US)

(*) Notice: Subject to any disclaimer, the term of this patent is extended or adjusted under 35 U.S.C. 154(b) by 0 days.

(21) Appl. No.: 15/986,696

(22) Filed: May 22, 2018

(51) Int. Cl.
| | | |
|---|---|---|
| H02G 7/06 | (2006.01) | |
| H02G 7/05 | (2006.01) | |
| F16L 3/14 | (2006.01) | |
| A61M 25/02 | (2006.01) | |
| A61M 16/08 | (2006.01) | |
| A61M 39/08 | (2006.01) | |

(52) U.S. Cl.
CPC .......... *A61M 25/02* (2013.01); *A61M 16/08* (2013.01); *A61M 39/08* (2013.01); *A61M 2205/0272* (2013.01); *A61M 2209/08* (2013.01); *F16L 3/14* (2013.01); *H02G 7/05* (2013.01); *H02G 7/06* (2013.01)

(58) Field of Classification Search
USPC ........................................ 248/58, 61, 62, 63
See application file for complete search history.

(56) References Cited

U.S. PATENT DOCUMENTS

| | | | | |
|---|---|---|---|---|
| 2,465,857 A | * | 3/1949 | Erling | F16L 3/00 248/61 |
| 3,085,775 A | * | 4/1963 | Crates | H01R 4/38 174/160 |
| 3,704,350 A | * | 11/1972 | Itoh | B66C 13/12 105/151 |
| 3,802,351 A | * | 4/1974 | Pascuzzi | B66C 13/12 104/112 |
| 3,832,976 A | * | 9/1974 | Sands | A01K 15/028 119/518 |
| 4,014,583 A | * | 3/1977 | Forbes | B60J 11/06 293/128 |

* cited by examiner

*Primary Examiner* — Alfred J Wujciak
(74) *Attorney, Agent, or Firm* — Gulf Coast Intellectual Property Group

(57) ABSTRACT

A tubing management apparatus that is operable to provide management of a medical tube. The tubing management apparatus includes a cord having a coiling device coupled to the first end of the cord and a clip secured to the second end of the cord. A plurality of couplers are slidably coupled to the cord intermediate the first end and second end. The plurality of couplers include a body having an upper portion and a lower portion. The upper portion of the body is configured to be slidably secured to the cord. The upper portion of the body of each of the plurality of couplers has an embedded magnet so as to assist in maintaining the couplers adjacent to each other. The lower portion of the body of the plurality of couplers includes various alternative embodiments that are configured to receive and retain a portion of a tube.

9 Claims, 3 Drawing Sheets

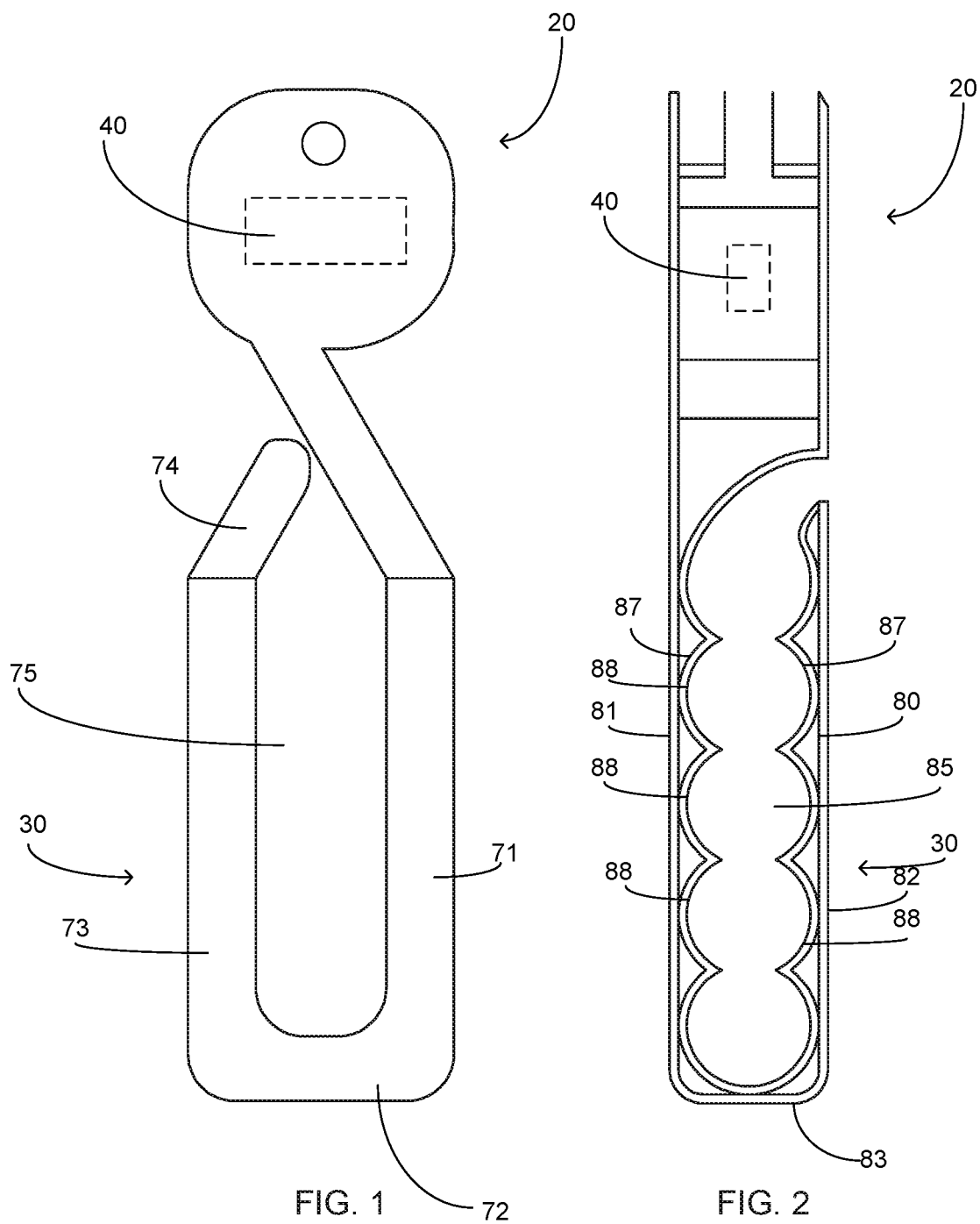

MEDICAL TUBING MANAGEMENT APPARATUS

FIELD OF THE INVENTION

The present invention relates generally to patient tube management apparatus, more specifically but not by way of limitation, a patient tube management apparatus that is operable to provide organization of tubing such as but not limited to oxygen or intravenuous tubing wherein the tube management apparatus is configured to utilize magnetic holders to control the deployment of the tubing operably coupled therewith.

BACKGROUND

Millions of patients are coupled to intravenous and/or oxygen tubing and machines either as part of post-surgical administration of medicinal therapy or for routine delivery of intravenously delivered drugs or oxygen supply. As is known in the art, intravenous delivery of drug compounds typically includes an intravenous pump and a tubing that is operably coupled thereto. Similarly, patient oxygen typically has a oxygen cylinder source that provides a supply of oxygen to a patient via tubing. Common insertion of the intravenous tubing can include but not be limited to subclavian taps or similar wherein a patient intravenous tubing is coupled to the aforementioned either continuously or temporarily as part of a drug treatment administration program.

The utilization of intravenous therapy can create physical challenges for a patient. Even only being operably coupled to the intravenous pump for a few hours results in physical limitations due to the requirement of cord management. Typically intravenous pumps are supplied with a substantial length of intravenous tubing to allow a patient a certain degree of movement. Supplying the typical length of intravenous tubing results in potential issues such as but not limited to tangling and kinking wherein the intravenous tubing can become entangled with various articles presenting risk for the patient operably coupled thereto. Patients operably coupled to medical oxygen face similar challenges to those coupled to intravenous tubing wherein the management of the tubing can be cumbersome.

Accordingly, there is a need for a medical tubing management apparatus that provides control and dispensing of medical tubing so as to provide improved management of the tubing while being operably coupled to a patient.

SUMMARY OF THE INVENTION

It is the object of the present invention to provide a medical tubing management apparatus that is configured to provide incremental dispensal and control of medical tubing that is operably coupled to a patient.

Another object of the present invention is to provide a medical tubing management apparatus that includes a main cord wherein the cord includes a first end and a second end.

A further object of the present invention is to provide a medical tubing management apparatus that further includes a plurality of couplers slidably secured to the main cord.

Still another object of the present invention is to provide a medical tubing management apparatus that is configured to provide incremental dispensal of intravenous tubing wherein the plurality of couplers include a body having an upper end and a lower end.

An additional object of the present invention is to provide a medical tubing management apparatus configured to provide improved management of medical tubing while operably coupled to a patient wherein the upper end of the body is configured to be releasably secured to an adjacent upper end.

Yet a further object of the present invention is to provide a medical tubing management apparatus that is configured to provide incremental dispense and control of medical tubing wherein the lower end of the body of the couplers has various alternative embodiments configured to receive and retain a portion of medical tubing.

Another object of the present invention is to provide a medical tubing management apparatus configured to provide improved management of medical tubing wherein the second end of the main cord is configured to be releasably secured to a patient.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

FIG. 1 is a side view of an embodiment of a coupler of the present invention; and FIG. 2 is a side view of an alternative embodiment of a coupler of the present invention.

DETAILED DESCRIPTION

Figures 3, 4:
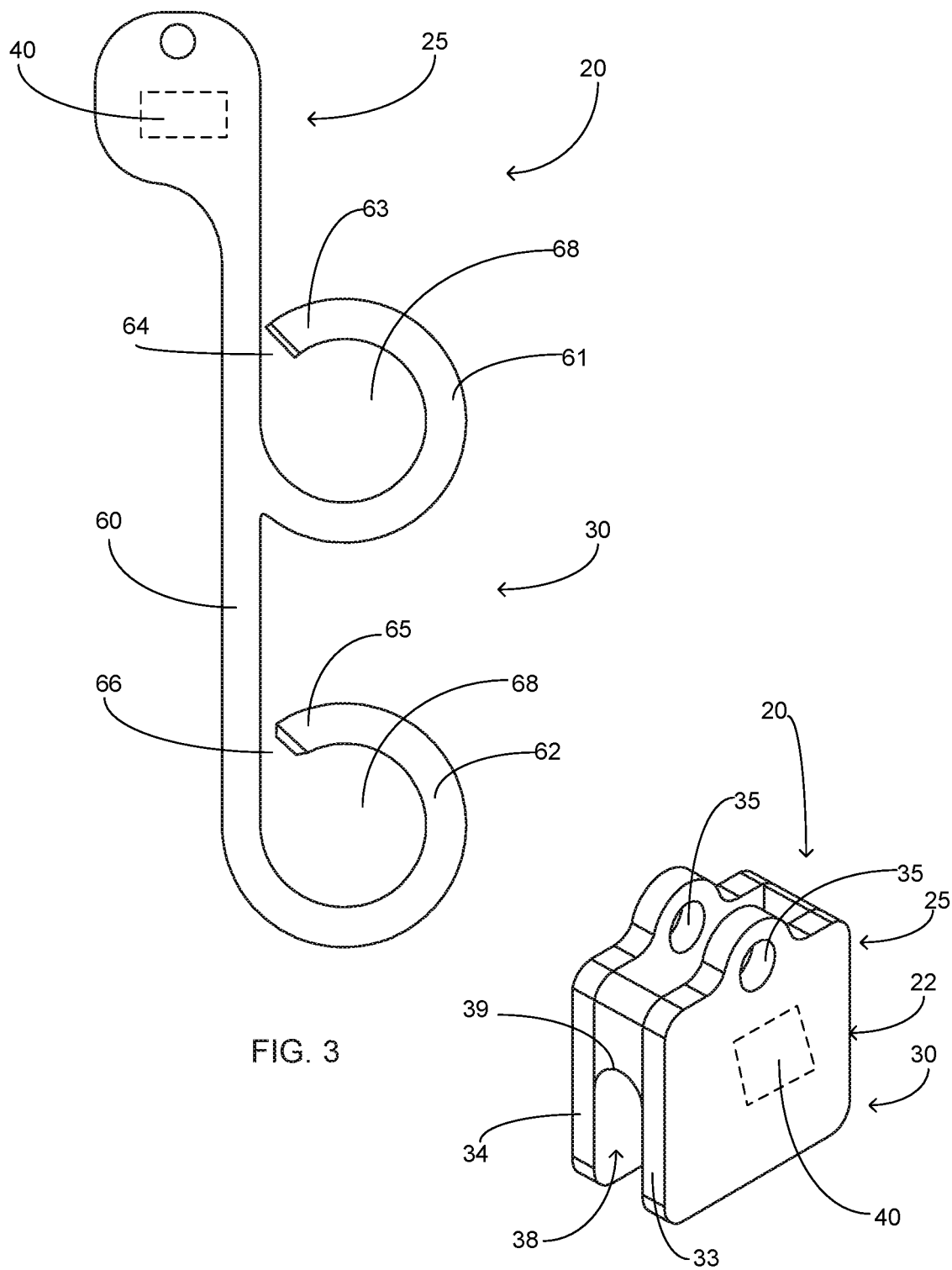
FIG. 3 is a side view of an alternative embodiment of a coupler of the present invention.
FIG. 4 is a perspective view of an alternative embodiment of a coupler of the present invention.

Referring now to the drawings submitted herewith, wherein various elements depicted therein are not necessarily drawn to scale and wherein through the views and figures like elements are referenced with identical reference numerals, there is illustrated a medical tubing management apparatus 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Figure 5:
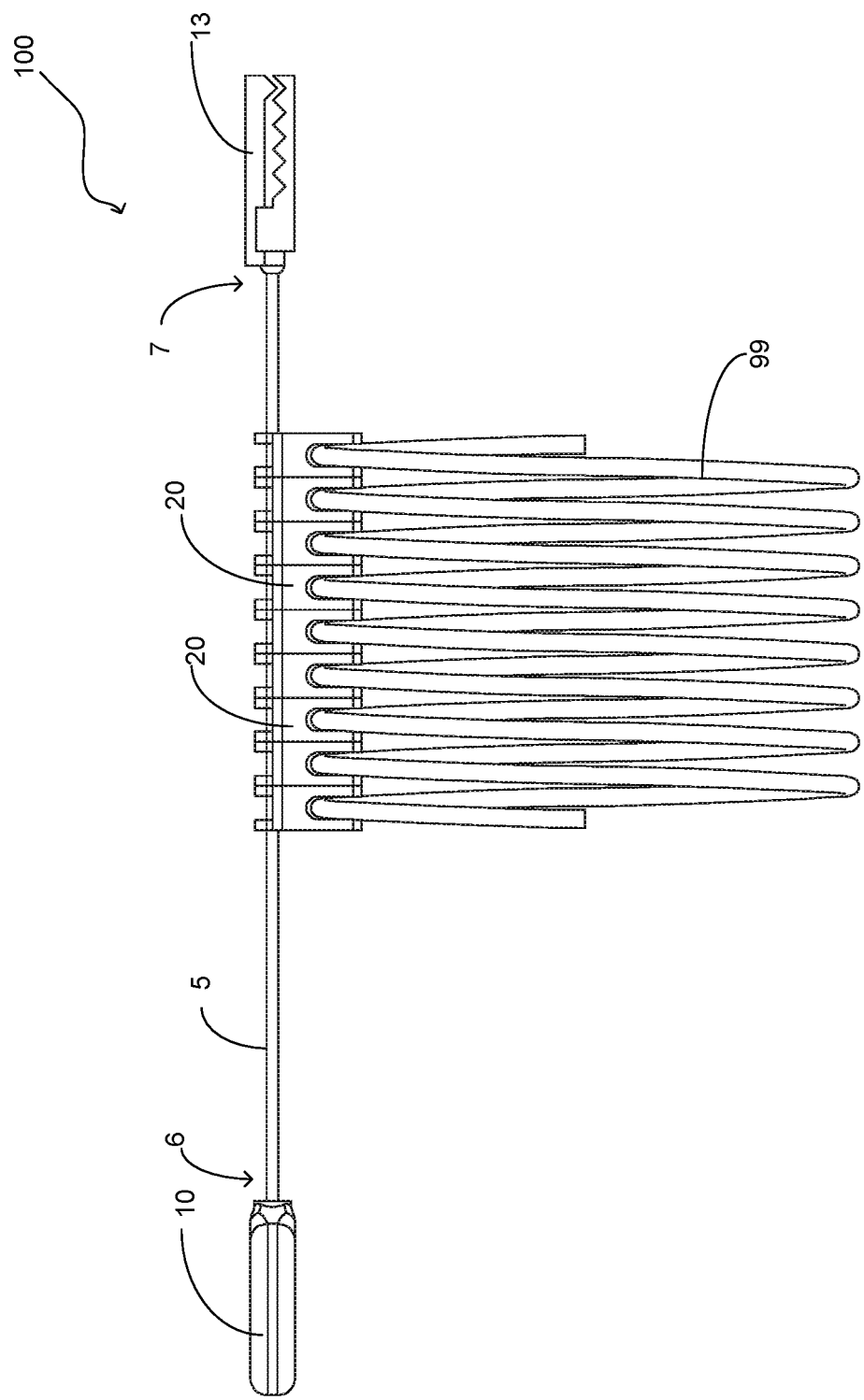
FIG. 5 is a side view of the intravenous tubing management apparatus.

Referring in particular to FIG. 5 herein, the medical tubing management apparatus 100 includes a cord 5 having a first end 6 and a second end 7. The cord 5 is manufactured from a suitable durable material and is operably wound on coiling device 10. Coiling device 10 is a conventional spring biased coiling device that is configured to provide storage of a portion of the cord 5 and is operable to provide extension and retraction thereof. It is contemplated within the scope of the present invention that the cord 5 could be provided in numerous alternate lengths. The cord 5 as will be further discussed herein has a plurality of couplers 20 slidably coupled thereto. While a coiling device 10 is illustrated herein, it is contemplated within the scope of the present invention that the medical tubing management apparatus 100 could be provided with a cord 5 of a fixed length and no coiling device 10 is operably coupled thereto. Secured to the second end 7 of the cord 5 is clip 13. Clip 13 is a conventional alligator clip that is operably to secure to an article such as but not limited to a patient gown. While a clip 13 is illustrated herein for providing a technique to releasably secure the second end 7 of the cord 5 to a patient, it is contemplated within the scope of the present invention that the second end 7 of the cord 5 could be provided with alternate elements so as to secure the second end 7 to a patient.

The medical tubing management apparatus 100 includes a plurality of couplers 20. The couplers 20 are configured to releasably retain a portion of exemplary medical tubing 99 therein. The couplers 20 include a body 22 being manufactured from a suitable durable material such as but not limited to plastic. The body 22 includes an upper portion 25 and lower portion 30 contiguously formed. The upper portion 25 is configured to be operably secured to the cord 5 and the lower portion 30 is configured to releasably secure a portion of medical tubing 99 therein. The couplers 20 are secured to the cord 5 and are adjacent to each other as illustrated herein in FIG. 5. Each adjacent coupler 20 has a portion of the medical tubing 99 operably secured thereto in order to provide a manageable configuration of the medical tubing 99 as illustrated in FIG. 5. The upper portion 25 of the body 22 includes apertures 35. Apertures 35 are formed in the upper portion 25 utilizing suitable techniques and are configured to have the cord 5 journaled therethrough so as to slidably secure the coupler 20 to the cord 5. It is contemplated within the scope of the present invention that the coupler 20 could have as few as one aperture 35 or more than one for securing to the cord 5. Furthermore, it is contemplated within the scope of the present invention that the couplers 20 could have alternate structures or elements configured to provide the ability to slidably secure the coupler 20 to the cord 20 in addition to or in conjunction with the apertures 35. The couplers 20 are movable intermediate a first position and a second position. FIG. 5 herein illustrates the first position of the couplers 20 wherein the couplers 20 are adjacent to each other and retained in this position via magnets 40. As a user requires additional length of the medical tubing 99, a slight force is applied to the intravenous tube 99 so as to release a coupler 20 and slidably traverse along the cord 5. This is executed for the number of couplers 20 required so as to deliver the desired length of medical tubing 99 closer to a user. While the couplers 20 are illustrated herein having a body 25 with lower portion 30 being suspended downward from upper portion 25, it is contemplated within the scope of the present invention that the body 25 could have portions extending in alternate directions either solely or in combination with the lower portion 30 that are configured to receive and secure medical tubing 99 therein. It should be understood that the body 25 could have an element configured to receive and secure a portion of medical tubing 99 wherein the element extends in alternate directions from the upper portion 25 such as but not limited to upward or laterally therefrom.

The body 22 has disposed therein proximate the upper portion 25 a magnet 40. The magnet 40 is operably to provide releasable securing of adjacent couplers 20 as shown in FIG. 5. The magnet 40 is provided having a suitable strength so as to secure the adjacent couplers 20 but allow separation thereof as a patient requires additional length of medical tubing 99. It is contemplated within the scope of the present invention that the magnet 40 could be provided in alternate sizes. Furthermore, it should be understood within the scope of the present invention that the couplers 20 could have more than one magnet 40 depending upon the structure of the body 22 of the coupler 20. The embodiment of the coupler 20 illustrated herein in FIG. 4 would include a magnet 40 on each opposing side 33,34 of the lower portion 30. While a magnet 40 is the preferred technique of releasably securing the couplers 20, it is contemplated within the scope of the present invention that the couplers 20 could utilize alternate materials and or structures to facilitate the releasable coupling of the couplers 20. By way of example but not limitation, a pressure sensitive adhesive or hook and loop material could be utilized on the couplers 20 to provide releasable securing thereof.

Referring in particular to the coupler 20 embodiment illustrated in FIG. 4 the lower portion 30 includes opposing sides 33, 34. Intermediate opposing sides 33,34 is void 38. Void 38 is bordered by top wall 39. The void 38 is formed having a suitable width wherein the void 38 can frictionally engage a portion of the medical tubing 99 and retain therein. The arcuate shape of the top wall 39 provides a mateable engagement with the shape of the medical tubing 99. While the void 38 is illustrated herein as having a specific depth, it is contemplated within the scope of the present invention that the void 38 have a depth sufficient to secure a portion of the intravenous tubing 99 therein. It should be understood within the scope of the present invention that the void 38 could be manufactured in alternate depths and still achieve the desired function described herein.

Illustrated herein in FIGS. 1, 2 and 3 are alternative embodiments of the coupler 20. Across the alternate embodiments of the coupler 20 the upper portion 25 of the body 22 is generally consistent having an aperture 35 configured to secure to the cord 5 and further including at least one magnet 40 embedded therein. It should be understood that the upper portion 25 could be manufactured from magnetic material instead of having a magnet disposed therein. The lower portion 30 illustrated in FIG. 3 includes an elongated support member 60 that extends downward from the upper portion 25. A first loop member 61 and a second loop member 62 are contiguously formed with the support member 60. The first loop member 61 includes end 63 wherein end 63 is adjacent support member 60 having a void 64 therebetween. The second loop member 62 is similarly formed having end 65 adjacent support member 60 with void 66 therebetween. The voids 64, 66 provide a technique to introduce a portion of the medical tubing 99 into the center 68 for securing thereof. While a first loop member 61 and a second loop member 62 are illustrated herein it is contemplated within the scope of the present invention that the lower portion 30 could have as few as one loop member or more than two loop members. The first loop member 61 and a second loop member 62 are formed so as to provide and alternate holding configuration of the medical tubing 99.

Now referring to FIG. 1 the lower portion 30 includes support members 71, 72, 73 and 74 integrally formed to create void 75. Support members 71, 72, 73 and 74 are contiguously formed utilizing suitable techniques and are manufactured from a material such as but not limited to plastic. The void 75 is of suitable length so as to accommodate therein several wounds of the medical tubing 99. Support member 74 is formed at an inward angle so as to ensure retention of the medical tubing 99 disposed within the void 75.

Referring to FIG. 2, the lower portion 30 of the coupler 20 includes support member 80. Support member 80 includes a left wall 81, a right wall 82 and a bottom 83 integrally formed to create center void 85. An opening 86 provides access to center void 85. Center void 85 includes inner walls 87 that include adjacent semicircular formations 88 that are configured to retain multiple wounds of the exemplary medical tubing 99. It is contemplated within the scope of the present invention that the lower portion 30 illustrated in FIG. 2 could have various quantities of the semicircular formations 88 in order to provide releasable securing of alternate quantities of wounds of the medical tubing 99.

The alternate embodiments of the lower portion 30 herein provide exemplary structures configured to retain the medical tubing 99. It is contemplated within the scope of the present invention that the lower portion 30 could be configured in alternate manners in order to achieve the desired objective of receiving and retaining a portion of the medical tubing 99. The embodiments illustrated herein do not serve to limit the structure of the lower portion 30 of the couplers 20. It should also be further understood that while an medical tube 99 has been discussed and illustrated herein it is contemplated within the scope of the present invention that the medical tubing management apparatus 100 could be utilized to provide management of various types of tubing and cords for many alternate applications.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A tube management apparatus comprising:
a cord, said cord having a first end and a second end;
a plurality of couplers, said plurality of couplers being slidably secured to said cord, each plurality of couplers having a body, said body of said plurality of couplers having an first portion and a second portion, said first portion being configured to be slidably secured to said cord, said second portion of said body being integrally formed with said first portion of said body and underneath said first portion, said second portion of body having opposing sidewalls extending downward therefrom, said opposing sidewalls forming a void, said void located underneath said second portion of said body, said void configured to have a portion of a tube disposed therein, said opposing sidewalls configured to bias against the portion of the tube disposed in said void, said second portion of said body configured to releasably secure a portion of the tube therein;
a plurality of keepers, said plurality of keepers being integrated into said first portion of said body of each of said plurality of couplers, said second portion having U-shaped channels integrally formed therein for retaining the portion of the tube, said plurality of keepers configured to attach and maintain said plurality of couplers in an adjacent configuration in a first position of the plurality of couplers; and
wherein the plurality of couplers are movable to a second position.

2. The tube management apparatus as recited in claim 1, wherein said plurality of keepers are magnets, said magnets being embedded within said first portion of said body.

3. The tube management apparatus as recited in claim 2, and further including at least one aperture, said at least one aperture being present in said first portion of said body, said at least one aperture configured to have said cord journaled therethrough, said at least one aperture operable to facilitate slidable securing of the plurality of couplers along said cord.

4. The tube management apparatus as recited in claim 3, and further including a clip, said clip being secured to said second end of said cord.

5. The tube management apparatus as recited in claim 4, and further including a coiling device, said coiling device being secured to said first end of said cord, said coiling device operable to provide extension and retraction of said cord.

6. The tube management apparatus as recited in claim 5, wherein in said second position a coupler releases from an adjacent coupler and slidably traverses along said cord.

7. A tube management apparatus configured to promote management and deployment of a tube comprising:
a cord, said cord having a first end and a second end;
a plurality of couplers, said plurality of couplers being slidably secured to said cord, each plurality of couplers having a body, said body of said plurality of couplers having an upper portion and a lower portion, said upper portion being configured to be slidably secured to said cord, said upper portion having at least one aperture, said at least one aperture having said cord journaled therethrough so as to suspendedly mount said plurality of couplers to said cord, said at least one aperture having said cord journaled therethrough being configured to provide slidable coupling of the plurality of couplers to said cord, said lower portion of said body configured to releasably secure a portion of a tube, said lower portion further including opposing sidewalls extending downward therefrom having a void therebetween, said opposing sidewalls operable to bias against the portion of the tube disposed in said void;

a plurality of keepers, said plurality of keepers being integrated into said upper portion of said body of each of said plurality of couplers, the lower portion of said body being u-shaped channels integrally formed therein for retaining the portion of the tube, said plurality of keepers configured to attach and maintain said plurality of couplers in an adjacent configuration in a first position of the plurality of couplers; and wherein the plurality of couplers are movable to a second position wherein the second position one of said plurality of couplers is slidably traversed along said cord.

8. The tube management apparatus as recited in claim 7, wherein said plurality of keepers are magnets, said magnets being embedded within said upper portion of said body.

9. The tube management apparatus as recited in claim 8, and further including a coiling device, said coiling device being secured to said first end of said cord, said coiling device operable to provide extension and retraction of said cord.

* * * * *